United States Patent [19]

Vidrine et al.

[11] Patent Number: 4,588,893
[45] Date of Patent: May 13, 1986

[54] LIGHT-PIPE FLOW CELL FOR SUPERCRITICAL FLUID CHROMATOGRAPHY

[75] Inventors: D. Warren Vidrine; Daniel R. Allhands, both of Madison, Wis.

[73] Assignee: Nicolet Instrument Corporation, Madison, Wis.

[21] Appl. No.: 704,739

[22] Filed: Feb. 25, 1985

[51] Int. Cl.$^4$ .............................................. G01N 21/05
[52] U.S. Cl. .................................... 250/428; 250/343; 356/246
[58] Field of Search .................. 250/428, 432 R, 437, 250/343, 373; 356/436, 437, 246; 350/96.28, 96.34

[56] References Cited

U.S. PATENT DOCUMENTS 3,524,709  12/1970  Hrdina ................................. 356/246
4,420,690  12/1983  Kuehl .................................. 250/428

OTHER PUBLICATIONS

Ohlmann et al., *J. Opt. Soc. America*, vol. 48, No. 8, Aug. 1958, pp. 531-533.
M. D. Erickson, "Gas Chromatography/Fourier Transform Infrared Spectroscopy Applications", Reprinted from Applied Spectroscopy Reviews, 15(2), pp. 261-325, (1969).
D. R. Gere, "Supercritical Fluid Chromatography", Science, 222, pp. 253-259, Oct. 21, 1983.
Brochure by Nicolet Instrument Corporation entitled "20 DXB/20 SXB Fourier Transform Infrared Spectrometer Series."

*Primary Examiner*—Alfred E. Smith
*Assistant Examiner*—Jack I. Berman
*Attorney, Agent, or Firm*—Isaksen, Lathrop, Esch, Hart & Clark

[57] ABSTRACT

A light-pipe flow cell (10) for high pressure fluids is disclosed which has a main support body (15) with a gold light-pipe element (22) mounted therein. Infrared transmissive windows (26, 27) are mounted to the main support body against sealing rings (31, 32) to seal off the polished central bore (23) of the light-pipe element from ambient atmosphere while allowing an infrared beam to be passed therethrough. Pressure plates (14, 18) are mounted to the main support body (15) to apply pressure to the windows over the sealing rings to tightly seal the windows without exerting undue stress thereon. Flow of liquid or supercritical fluid from a chromatography column is directed through inlet channels (35, 38) in the support body and light-pipe element to one end of the light-pipe bore (23) and out of the opposite end of the bore through a channel (41) in the light-pipe element and a communicating channel (36) in the main support body. The flow cell (10) may be connected in a supercritical fluid chromatography system wherein effluent from the chromatography column (64) is passed through the flow cell (10) and is subjected to an infrared beam to allow infrared spectrometric analysis.

19 Claims, 6 Drawing Figures

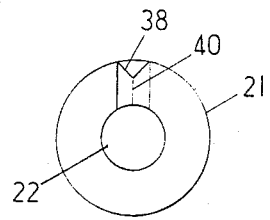
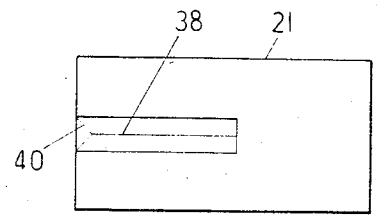
FIG. 3   FIG. 4
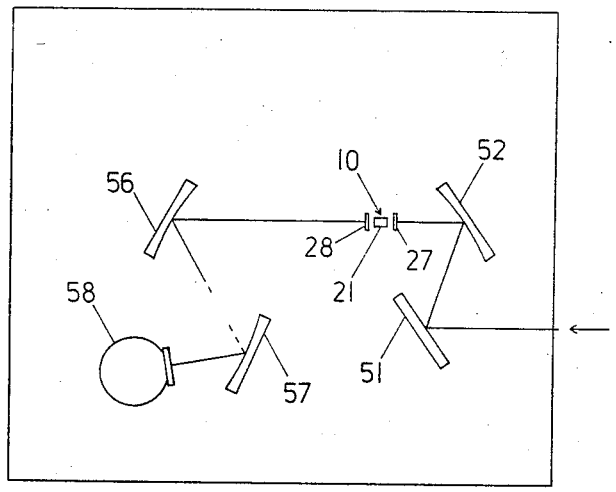
FIG. 5
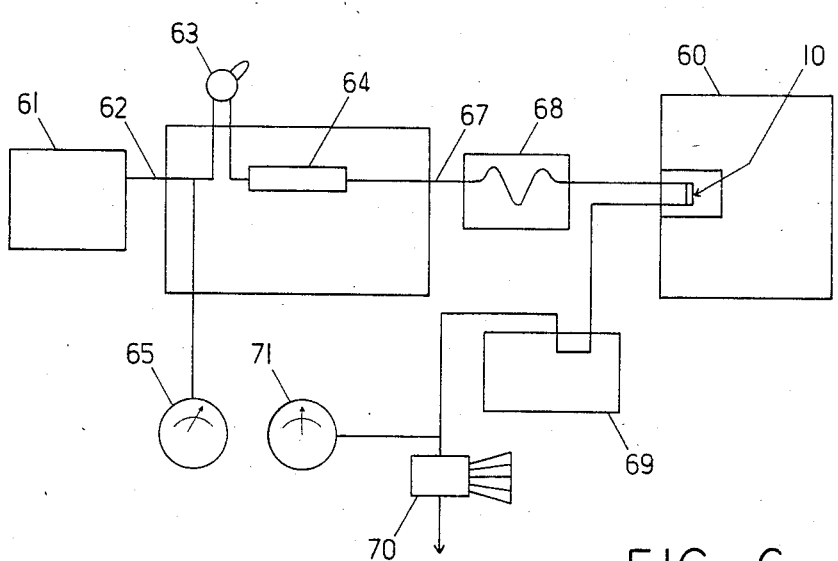
FIG. 6

LIGHT-PIPE FLOW CELL FOR SUPERCRITICAL FLUID CHROMATOGRAPHY

TECHNICAL FIELD

This invention pertains generally to the field of spectrometry and particularly to systems for infrared spectrometric analysis of samples obtained by supercritical fluid chromatography.

BACKGROUND OF THE INVENTION

The combination of gas or liquid chromatography with infrared spectrometry has become widely used in chemical analysis. In particular, gas chromatography has been combined with Fourier transform infrared spectrometry to provide sensitivity levels and scanning speed which are superior to that obtainable with gas chromatography infrared spectrometry using dispersive instruments. Although the effluent from the gas chromatography column can be trapped and held for analysis, more commonly the stream is passed continuously through a light-pipe flow cell where an infrared beam passes through the flowing gas. The exiting infrared beam is then detected and analyzed.

The typical gas chromatograph flow cell accessory used in Fourier transform infrared spectrometry is a hollow tube or light-pipe with infrared transparent windows sealed to the ends of the tube. The characteristics of the light-pipe are crucial to the performance of the system. It is generally desirable to maximize the number of sample molecules that are in the infrared beam path while minimizing the radiation loss due to reflection and absorbence. The material in the light-pipe which contacts the gas must also be non-reactive. The light-pipes used in commercial instrumentation to meet these requirements are typically cylindrical glass tubes which have a thin coating of gold deposited on the inner surface. Gold is used because it is reflective, stable and inert. The glass light-pipes are surrounded and protected by a holder typically formed of metal, such as stainless steel. Infrared transmissive windows (e.g., potassium bromide) are mounted to either the ends of the light-pipe or to the holder with seals which seal off the ends of the light-pipe to prevent escape of the gases.

More recently, chromatography has been carried out utilizing supercritical fluids. Supercritical fluids have many attributes which allow high performance chromatography, including low mobile phase viscosity, high analyte diffusivity, and good solubility for a wide range of analytes. In addition, the observed chromatographic characteristics can be affected by changing the density of the mobile phase by changing the temperature or the pressure or both. Thus, a single supercritical mobile phase can be used to obtain a wide variety of separations without the time consuming column equilibration necessary in high performance liquid chromtography when changing mobile phase composition. Carbon dioxide is the most commonly used mobile phase in supercritical fluid chromatography.

Adequate detection has proven to be a significant instrument problem with supercritical fluid chromatography. Ultraviolet detection has been most commonly used to present, since many supercritical fluid chromatography phases are transparent in the ultraviolet region and most analytes studied contain ultraviolet chromophores. Flame ionization and fluorescence detection with capillary columns have also been used. However, these systems provide for essentially universal detection rather than specific detection. Fourier transform infrared spectrometry could yield both types of detection in real time, advantages which had been achieved with relatively high sensitivity in both gas chromatography and high pressure liquid chromatography. However, the conventional light-pipes used in gas chromatography Fourier transform infrared spectrometry or in liquid chromatography cannot be used for supercritical fluid chromatography because of the high operating pressures of the supercritical fluid.

SUMMARY OF THE INVENTION

In accordance with the present invention, a light-pipe flow cell is constructed to withstand readily the very high pressures utilized in supercritical fluid chromatography while providing a highly transmissive path for the infrared beam, minimal disruption of fluid flow passing through the light-pipe, and minimization of dead volume in the light-pipe to provide maximum utilization of the light-pipe length. The flow cell can be incorporated in supercritical fluid chromatography systems to allow Fourier transform infrared spectrometry on the fluid flowing in the cell. Very high infrared throughput is obtained, providing a high signal-to-noise ratio.

The flow cell structure of the invention includes a main support body having a bore therein with a light-pipe element inserted in the bore and tightly engaged with the wall thereof. The light-pipe element, preferably formed of gold, has a central cylindrical bore with a polished and reflective interior wall, and has channels formed therein which extend from inlet and outlet openings on either end of its bore to inlet and outlet channels formed in the main support body through which fluid flows in and out of the structure. Infrared transmissive window elements are mounted at each end of the bore of the light-pipe and are each pressed against a resilient sealing ring mounted in a groove in the support body which surrounds the light-pipe element. A pressure plate having a central opening is mounted over each window element and secured to the support body to press the window elements tightly against the sealing rings. A central opening in each pressure plate allows the infrared beam to pass through the window elements into the bore of the light-pipe element and out again to an infrared detector. The mounting of the sealing rings to the main support body and the position of the window elements with respect thereto is such that the inner face of each window element is very near to or in light contact with the end of the light-pipe element but is not sealed thereto so that the windows do not apply substantial pressure to the light-pipe element itself.

Because a window element is used having much larger dimensions than the bore of the light-pipe element, the pressure between the sealing rings and the window can be distributed over a relatively large peripheral area outside of the central opening in the pressure plates, thereby allowing the pressure plates to be pressed with high force against the sealing ring without directly applying substantial force to the inner light-pipe element itself. This distribution of force imposes no stress on the light-pipe element and prevents the localization of high stresses in the windows. The light-pipe element is in tight, press-fit engagement with the main support body, preventing any transfer of fluid at the joint between the light-pipe element and the main body. The inlet and outlet openings in the light-pipe element bore are preferably formed at the extreme ends thereof, such that no dead space in the light-pipe exists in which fluid is not continually flowing, thereby maximizing utilization of the entire length of the light-pipe bore.

The bore of the light-pipe element is formed to be relatively narrow and short relative to light-pipes used in standard Fourier transform infrared (FTIR) spectrometry. By utilizing FTIR refocusing optical systems modified to suit the internal diameter and length of the light-pipe bore, very high infrared throughputs are obtained.

Further objects, features, and advantages of the invention will be apparent from the following detailed description taken in conjunction with the accompanying drawings.

BRIEF DESCRIPTION OF THE DRAWINGS

In the drawings:

FIG. 3 is an end view of the light-pipe element portion of the flow cell of FIG. 1.

FIG. 4 is a top view of the light-pipe element.

FIG. 5 is a schematic view illustrating the infrared beam optical focusing elements and detector.

FIG. 6 is a schematic diagram of a supercritical fluid chromatography system with Fourier transform infrared spectrometric detection utilizing the flow cell of the invention.

DESCRIPTION OF THE PREFERRED EMBODIMENT

Figure 2:
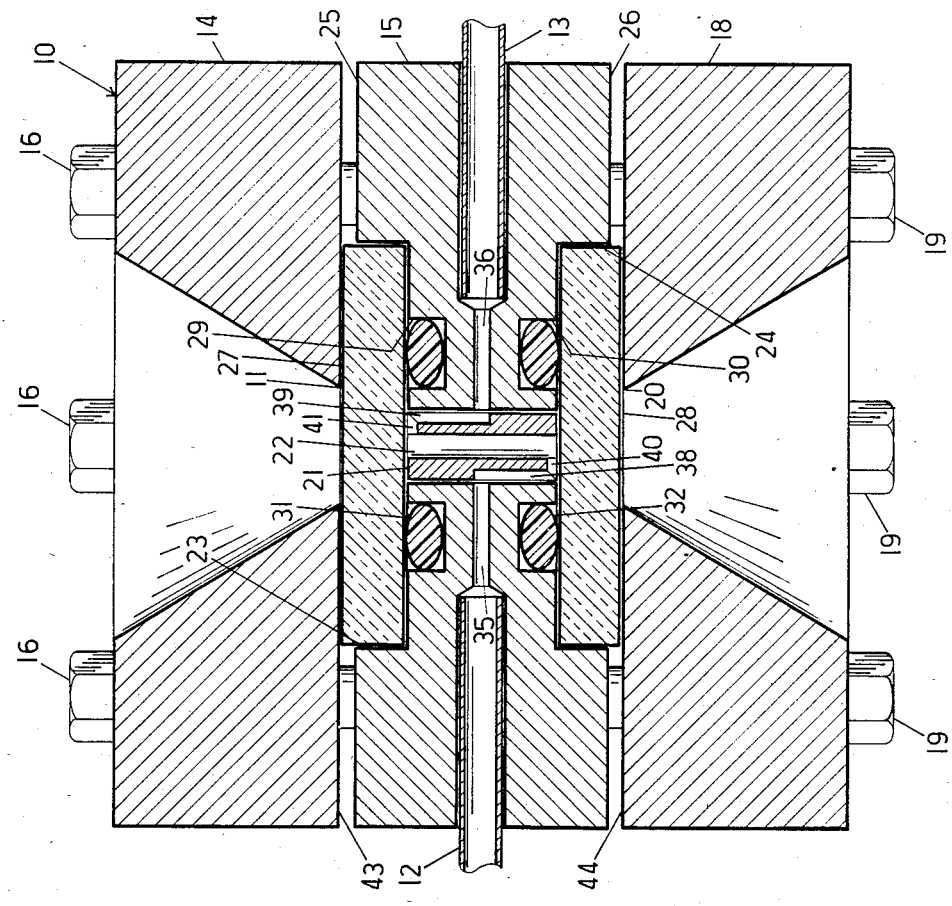
FIG. 2 is a cross-section of the flow cell taken generally along the lines 2—2 of FIG. 1.
Figure 1:
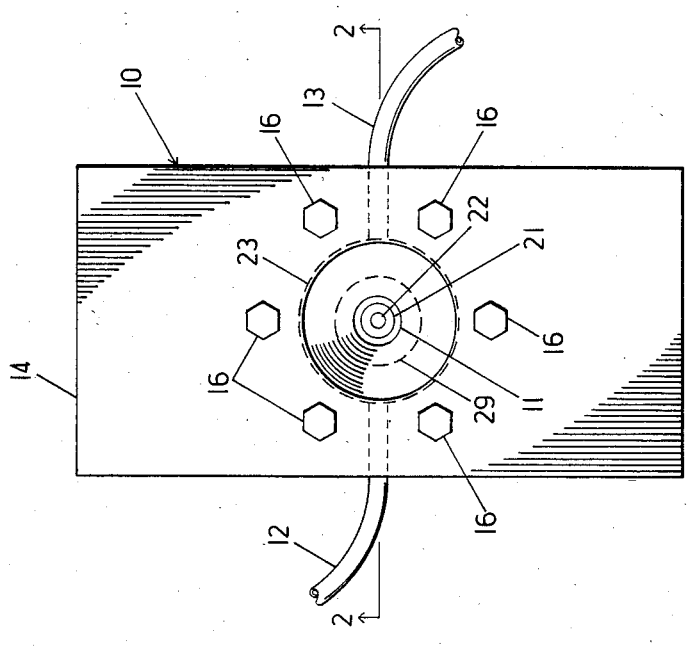
FIG. 1 is a plan view of the flow cell of the invention looking toward the infrared beam entrance window.

With reference to the drawings, a flow cell adapted for use in supercritical fluid chromatography is shown generally at 10 in FIG. 1 looking toward the entrance opening 11 into which the infrared beam may enter the flow cell. Supercritical fluid flows into the flow cell through an inlet tube 12 and out through an outlet tube 13. The entrance opening 11 is defined by a generally circular opening at the bottom of a cone-shaped pit formed in a first pressure plate 14 which is mounted to a main support body 15, as shown in FIG. 2, by bolts 16 which thread into the main support body at points spaced about the entrance opening 11. A similar pressure plate 18 is mounted to the main support body 15 by several bolts 19 which pass through the plate 18 and thread into the main body 15 at points spaced about the flow cell exit opening 20 from which the infrared beam passes out of the flow cell to a detector.

The main support body 15 has a central cylindrical bore, generally aligned with the entrance opening 11 and exit opening 20, into which a light-pipe element 21 is inserted. The light-pipe element 21 has a generally cylindrical outer periphery which closely matches the dimensions of the bore in the support body 15 and is tightly pressed fit into engagement with the bore. The light-pipe element 21 has a central cylindrical bore 22 which is polished longitudinally to reflect infrared light passing therethrough. Circular cylindrical indentations 23 and 24 are formed on the opposite sides 25 and 26, respectively, of the main support body 15 and are sized to receive infrared transmissive, disc-shaped window elements 27 and 28. Circular grooves 29 and 30 are formed in the bottom of the indentations 23 and 24, respectively, each surrounding the position of the light-pipe element 21. Elastomeric sealing rings 31 and 32, respectively, are seated in the grooves 29 and 30 and are compressed by the window elements 27 and 28 as they are pressed inwardly under the force of the pressure plates 14 and 18, thereby sealing off the interior bore of the light-pipe element 21 from the ambient atmosphere.

The inlet tube 12 and outlet tube 13, both preferably formed of stainless steel, are inserted into cylindrical holes drilled in the main support body 15 on opposite sides of the bore therein and are brazed into place, preferably utilizing silver solder. The end of the inlet tube 12 communicates with an inlet channel 35 drilled in the main support body which extends to an opening on the outer periphery of the light-pipe element, and a similar outlet channel 36 extends from the end of the outlet tube 13 through the main support body 15 to the periphery of the light-pipe element 21 at a position opposite that at which the channel 35 meets the element. The inlet channel 35 opens into communication with a groove 38 formed in the outer surface of the cylindrical light-pipe element which, with the wall of the bore in the main support body, defines a channel extending to an inlet opening 40 at one extreme end of the light-pipe bore 22. Similarly, the outlet channel 36 is in communication with a groove 39 which, with the wall of the bore in the main support body, defines a channel extending to an outlet opening 41 at the extreme opposite end of the light-pipe bore 22. The preferred form of the grooves which define the inlet and outlet channels in the light-pipe element 21 are illustrated in FIGS. 3 and 4. The groove 38 is preferably formed in a V-shape extending to a radial V-shaped channel 40 defining the inlet to the light-pipe bore 23. The outlet channel 39 is formed identically on the opposite side of the cylindrical light-pipe member 22 and extends to the outlet 41. The inlet and outlet channels 35 and 36 in the main support body preferably extend, as shown in FIG. 2, generally through the center of the body and spaced well away from the grooves 29 and 30.

The liquid or supercritical fluid flowing through the flow cell will be at very high pressures, typically in the range of 1,000 to 2,000 pounds per square inch (psi). For example, the critical pressure for carbon dioxide is 1073 psi at its critical temperature of 31° C. The fluid carrier phase and the chemicals carried therewith may be reactive or corrosive. Thus, the flow cell 10 must be capable of handling fluids at great pressure without leakage or damage and without reacting with any of the components of the fluid. The main support body 15 is thus preferably formed of a non-reactive metal (e.g., 304 stainless steel) and the light-pipe insert member 21 is preferably formed of gold or a gold alloy (e.g., 18-carat gold). The sealing O-rings 31 and 32 are preferably formed of polyperfluorinated elastomers (e.g., sold by DuPont under the trademark Kalrez). As examples of dimensions which have been found suitable for obtaining high infrared throughput in supercritical fluids, the light-pipe element 21 may have an interior bore 22 approximately 1 millimeter (mm) in diameter and 5 mm long and an external diameter of approximately 2.54 mm. The flow cell window element disks 27 and 28 must combine the characteristics of substantial transparency to infrared radiation and good structural strength since they will be exposed to the high pressures within the light-pipe bore 22. Suitable elements for the cell windows may be formed of zinc selenide with exemplary dimensions of 13 mm diameter by 2 mm thickness for a light-pipe element 21 having the aforementioned dimensions.

The light-pipe bore 22 is substantially shorter and narrower than the bores of typical light-pipes utilized in gas chromatography. The high density of the liquid or supercritical fluid flowing through the light-pipe, and the correspondingly high infrared absorbence of the fluid, dictates relatively small dimensions for the light-pipe bore. Since the volume of the bore 22 through which the fluid passes is relatively small, it is important that the amount of dead volume through which the fluid is not continuously flowing be minimized. In accordance with the present invention, the fluid inlet 40 into the light-pipe bore 22 is at one extreme end of the bore, directly adjacent to the inner face of the window 28, and the outlet 41 is at the other extreme end of the bore 22, immediately adjacent the other window 27. Thus, virtually no portion of the bore 22 will contain fluid which is not continuously flowing. To minimize the entrapment of any fluid from one portion of the material eluted from the chromatography column which might mix with subsequent samples, the light-pipe insert element 22 is preferably formed to be in tight, press-fit engagement with the cylindrical wall of the central bore in the main support body 15 so that no fluid can pass between the light-pipe element and the walls of the bore. Because both the light-pipe element 21 and the main body 15 are formed of metal (as contrasted with a glass light-pipe in a metal holder), tight engagement of the light-pipe element and main body can be maintained without damage to either during thermal expansions and contractions.

It is also preferred that the window elements 27 and 28 cooperate with the sealing rings 31 and 32 such that the inner faces of each window contacts but does not press hard against the bottom of the indentations 23 and 24. Only a very small amount of fluid will seep outwardly beyond the bore 22 of the light-pipe element and this flow will be blocked by the sealing rings 31 and 32. For purposes of illustration, the rings 31 and 32 have been shown compressed to an oval shape in FIG. 2, but it is understood that under full compression they will substantially occupy the grooves 29 and 30, preventing seepage of fluid into the grooves. The pressure plates 14 and 18 are preferably formed such that the edges of the openings 11 and 20 therein are just inward of the position of the sealing rings 31 and 32 so that force is applied by the plates 14 and 18 to the window elements 27 and 28 directly over the sealing rings. Since the sealing rings are seated in the grooves 29 and 30 formed in the main support body 15 at positions outwardly of the light-pipe bore 22, the openings 11 and 20 can be made wider than the bore of the light-pipe or even wider than the light-pipe element 21. By compressing the window elements 27 and 28 against the seals 31 and 32 in this manner, only compressive stress is applied to the material of the windows, which are generally capable of withstanding substantial compressive stress but would be vulnerable to sheer stresses as would exist if forces were applied to the windows at positions only outside of the sealing rings 31 and 32. The force applied by the pressure plates 14 and 18 to the window elements 27 and 28 can be controlled and evenly distributed by selectively tightening the bolts 16 and 19 to a desired torque level. Preferably, the window elements 27 and 28, when resting in the indentations 24 and 25, will have their outer faces extending above the adjacent faces of the main support body 15 so that the flat inner faces 43 and 44 of the pressure plates 14 and 18 do not contact the main support body 15 and rather transmit all the force applied thereby to the windows 27 and 28, thereby readily allowing the pressure applied to the windows 26 and 27 to be evenly distributed. Naturally, the pressure at the inner face between the windows 26 and 27 and the sealing rings 31 and 32 must be greater than the pressure applied by the fluid flowing through the flow cell.

The relative position of the flow cell 10 in the infrared optical path is illustrated in FIG. 5. The infrared beam 50 impinges on a flat mirror 51 and is reflected to a first off axis paraboloid mirror 52 (e.g., 70° off axis paraboloid, 3.5 inches (8.9 cm) effective focal length) mounted to focus the infrared beam at the input window element 27 of the flow cell 10. The infrared emerging from the exit window element 28 is collected by an off axis paraboloid mirror 56 (e.g., 60° off axis paraboloid, 9.33 inches (23.7 cm) effective focal length, mounted 9.33 inches (23.7 cm) from the exit window element 28) which focuses the beam on another off axis paraboloid mirror 57 (e.g., 70° off axis paraboloid, 3.5 inches (8.9 cm) effective focal length) which focuses the beam on an infrared detector 58, which may be a standard mercurycadmiumtelluride (MCT) detector. This arrangement provides for high infrared throughput with a light-pipe having the relatively small bore dimensions noted above (i.e., 1 mm diameter by 5 mm length).

As illustrated in FIG. 6, the light-pipe flow cell 10 may be mounted with the optical system of FIG. 5 as part of a Fourier transform infrared spectrometry apparatus, designated schematically at 60 in FIG. 6, incorporated with a supercritical fluid chromatography system. The commercially available chromatography system (for example, a Hewlett-Packard Model 1082B Liquid Chromatograph modified for supercritical fluid chromotography) includes a supercritical fluid pressure pump 61 supplying the fluid medium on a line 62 to an injector 63 which supplies a chromatography column 64. The pressure at the input line 62 is monitored by a pressure gauge 65. The effluent from the column 64 in the supercritical fluid carrier phase is supplied on line 67 through a passive heat exchanger 68 to the light-pipe flow cell 10, and the fluid may then be passed through an ultraviolet absorbence detector 69, if desired, before being vented to atmosphere through a back pressure regulator 70. The pressure at the outlet is monitored by a pressure gauge 71. This system allows the chemical sample from the column to be analyzed utilizing standard Fourier transform infrared spectrometry techniques.

It is understood that the invention is not confined to the particular embodiment herein illustrated and described, but embraces such modified forms thereof as come within the scope of the following claims.

What is claimed is:

1. A light-pipe flow cell adapted for use in supercritical fluid chromatography comprising:
   (a) a main support body having opposite sides and a bore extending therethrough from one side to the other side, and inlet and outlet channels formed in the main support body extending to openings into the bore therein;
   (b) a light-pipe element inserted in the bore in the main support body and tightly engaged with the walls thereof, the metal light-pipe element having a cylindrical bore therethrough with a polished and reflective interior wall, the light-pipe element having one channel formed therein extending from communication with the inlet channel in the main support body to an inlet opening at one end of the bore of the light-pipe element and having another channel formed therein extending from communication with the outlet channel in the main support body to an outlet opening at the opposite end of the bore of the light pipe element;

(c) two light transmissive window elements positioned at the opposite sides of the main support body over the light-pipe element and each extending outwardly beyond the light-pipe element over the sides of the main support body;

(d) resilient sealing means mounted between each window element and the main support body and engaged by the window elements for sealing off the bore of the light-pipe element from the ambient atmosphere; and (e) means for applying force to each window element at positions over the resilient sealing means.

2. The flow cell of claim 1 wherein the light-pipe element is formed of a gold alloy having a cylindrical outer surface which is tightly press-fit to a cylindrical bore in the main support body and wherein the channels in the light-pipe element are formed as grooves on opposite peripheral sides of the light-pipe element which extend, respectively, from the inlet and outlet channels in the main support body to the opposite ends of the cylindrical light-pipe element and thence inwardly to the inlet and outlet openings in the bore of the light-pipe element.

3. The flow cell of claim 1 wherein the window elements are formed as circular disks having flat opposite faces and of a material transmissive to infrared radiation.

4. The flow cell of claim 3 wherein the window elements are formed of zinc selenide.

5. The flow cell of claim 4 wherein the bore of the light-pipe element is approximately 5 millimeters long and 1 millimeter in diameter.

6. The flow cell of claim 1 wherein the sealing means comprises two sealing rings of polyperfluorinated elastomer, each seated in a circular groove formed in each side of the main support body surrounding the light-pipe element.

7. The flow cell of claim 1 wherein the window elements are formed as circular disks having flat opposite faces and wherein the main support body has circular cylindrical indentations in the opposite sides thereof with the light-pipe element extending from the bottom of one of the indentations to the other and wherein the window disk elements are mounted in the indentations in the sides of the main support body, and wherein the sealing means between each window and the main support body comprises an elastomer sealing ring seated in a circular groove in the bottom surface of each indentation in the main support body with each window disk element being pressed thereagainst to seal off the bore of the light-pipe element from the ambient atmosphere.

8. The flow cell of claim 7 wherein the means for applying force to the window elements comprises a pressure plate on each side of the main body, each pressure plate having a flat inner surface in contact with the outer face of the adjacent window element and a central opening therein which is positioned over the adjacent end of the light-pipe element, and including means for mounting the pressure plates to the main support body to allow selective application of force to each pressure plate at points about the central opening therein to allow force to be applied by each pressure plate uniformly to the adjacent window element at positions on the window element above the sealing ring.

9. The flow cell of claim 8 wherein the means for mounting the pressure plates to the main support body comprises, for each pressure plate, a plurality of bolts extending through the pressure plate and threaded to the main support body to thereby allow the distribution of force applied by the pressure plate to the window element to be adjusted by selectively tightening the bolts.

10. The flow cell of claim 1 wherein the main support body is formed of stainless steel, the window elements are formed of infrared transmissive zinc selenide, and the light-pipe element is formed of a gold alloy.

11. The flow cell of claim 1 wherein the internal bore of the light-pipe element is approximately 5 millimeters long and 1 millimeter in diameter.

12. A light-pipe flow cell adapted for use in supercritical fluid chromatography comprising:

(a) a metal main support body having opposite sides and a cylindrical bore extending therethrough from one side to the other side, a circular groove formed in each of the opposite sides of the main support body surrounding the position of the bore therein, and inlet and outlet channels formed in the main support body extending to openings in the bore therein;

(b) a cylindrical light-pipe element formed of a gold alloy inserted in the bore in the main support body and in tight, press-fit engagement with the wall of the bore in the main support body, the light-pipe element having a cylindrical bore therethrough with a polished and reflective interior wall, an inlet opening in the wall of the bore at one end thereof and an outlet opening in the bore at the opposite end thereof, and channels defined by grooves extending from, respectively, the inlet opening in the light-pipe element bore to the inlet channel in the main support body and from the outlet opening in the light-pipe element bore to the outlet channel in the support body;

(c) two infrared transmissive window elements formed as circular disks having flat opposite faces positioned respectively at the opposite sides of the main body over the light-pipe element and extending outwardly beyond the light-pipe element and over the circular groove in each side of the main support body;

(d) two sealing rings formed of a resilient elastomer material, each seated in a circular groove in one side of the main support body and extending upwardly to engage and be pressed by the adjacent window element;

(e) two pressure plates mounted to the opposite sides of the main support body, each pressure plate having a flat inner surface in contact with the outer face of the adjacent window element and a central opening therein which is positioned over the adjacent end of the light-pipe element; and (f) means for mounting the pressure plates to the main support body to allow selective application of force to each pressure plate at points about the central opening therein to allow force to be applied by each pressure plate uniformly to the adjacent window element at positions on the window element above the sealing ring such that each window is tightly pressed against the sealing ring to seal off the bore of the light-pipe element from the ambient atmosphere.

13. The flow cell of claim 12 wherein the window elements are formed of zinc selenide.

14. The flow cell of claim 12 wherein the internal bore of the light-pipe element is approximately 5 mm long and 1 mm in diameter.

15. The flow cell of claim 12 wherein the sealing rings are formed of polyperfluorinated elastomer.

16. The flow cell of claim 12 wherein the main support body has a circular cylindrical indentation in each of the opposite sides thereof with the light-pipe element extending from the bottom of one of the indentations to the other, and wherein the disk-shaped window elements are sized to fit the indentations in the sides of the main support body and are seated therein with the outer face of each window element extending outwardly beyond the main support body to allow engagement by the pressure plates.

17. The flow cell of claim 12 wherein each pressure plate has a cone-shaped depression therein which narrows from the outer face thereof to the opening therein.

18. The flow cell of claim 12 wherein the means for mounting the pressure plates to the main support body comprises, for each pressure plate, a plurality of bolts extending through the pressure plate and threaded to the main support body to thereby allow the distribution of force applied by the pressure plate to the window element to be adjusted by selectively tightening the bolts.

19. The flow cell of claim 12 wherein the main support body is formed of stainless steel, the window elements are formed of zinc selenide, and the sealing rings are formed of a polyperfluorinated elastomer.

* * * * *